United States Patent [19]

Breuer et al.

[11] 4,142,045
[45] Feb. 27, 1979

[54] CARBAMOYLALKYLUREIDO CEPHALOSPORINS

[75] Inventors: Hermann Breuer; Uwe D. Treuner, both of Regensburg, Fed. Rep. of Germany

[73] Assignee: E. R. Squibb & Sons, Inc., Princeton, N.J.

[21] Appl. No.: 876,789

[22] Filed: Feb. 10, 1978

Related U.S. Application Data

[62] Division of Ser. No. 714,420, Aug. 16, 1976, Pat. No. 4,086,422.

[51] Int. Cl.² .................. C07D 501/36; C07D 501/34; C07D 501/44
[52] U.S. Cl. ........................ 544/21; 544/24; 544/25; 544/26; 544/27; 544/28
[58] Field of Search ................ 544/21, 24, 25, 26, 544/27, 28

[56] References Cited

U.S. PATENT DOCUMENTS 3,932,392   1/1976   Johnson et al. .......... 544/30
3,935,204   1/1976   Dahlen et al. .......... 424/246

Primary Examiner—Paul M. Coughlan, Jr.
Assistant Examiner—David E. Wheeler
Attorney, Agent, or Firm—Lawrence S. Levinson; Merle J. Smith; Stephen B. Davis

[57] ABSTRACT

Carbamoylalkylureido cephalosporins of the formula

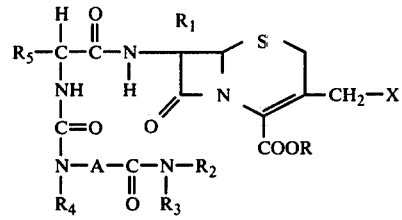

wherein R is hydrogen, lower alkyl, phenyl-lower alkyl, diphenyl-lower alkyl, tri(lower alkyl)silyl, trihaloethyl, a salt forming ion, or the group

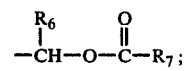

$R_1$ is hydrogen or methoxy; A is straight or branched chain alkylene of 1 to 6 carbons; $R_2$ and $R_3$ are independently selected from hydrogen and straight chain alkyl of 1 to 4 carbons, or $R_2$ is hydrogen and $R_3$ is branched chain alkyl of 3 or 4 carbons, phenyl, benzyl or phenethyl, or $R_2$ and $R_3$ taken together with N atom to which they are attached form

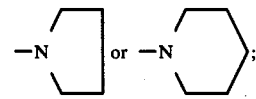

$R_4$ is hydrogen or lower alkyl; $R_5$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_6$ is hydrogen or lower alkyl; $R_7$ is lower alkyl; and X is hydrogen, lower alkanoyloxy,

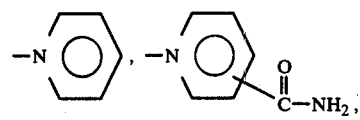

or certain heterothio groups; are disclosed. These compounds are useful as antibacterial agents.

7 Claims, No Drawings

CARBAMOYLALKYLUREIDO CEPHALOSPORINS

This is a division of application Ser. No. 714,420, filed Aug. 16, 1976 now U.S. Pat. No. 4,086,422.

BACKGROUND OF THE INVENTION

Cephalosporins having a ureido acyl side chain are disclosed in U.S. Pat. Nos. 3,673,183; 3,708,479; 3,833,568; and 3,860,591. Cephalosporins having various acyl side chains and a 7α-methoxy substituent are taught in various U.S. patents including U.S. Pat. Nos. 3,775,410; 3,780,031; 3,780,033; 3,780,034; 3,780,037; 3,843,641; etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to new carbamoylalkylureido-7α-methoxy or desmethoxy cephalosporin derivatives of the $$R_5-\overset{H}{\underset{NH}{C^*}}-\overset{O}{\underset{}{C}}-\overset{R_1}{\underset{H}{N}}\underset{O}{\overset{S}{\underset{N}{\bigsqcup}}}CH_2-X. \quad (I)$$
$$\overset{|}{C=O}$$
$$\overset{|}{N}-A-\overset{O}{\underset{||}{C}}-\overset{R_3}{\underset{|}{N}}$$
$$\overset{|}{R_4}\quad\quad R_2$$

R represents hydrogen, lower alkyl, phenyl-lower alkyl, diphenyl-lower alkyl, tri(lower alkyl)silyl, trihaloethyl, a salt forming ion, or the group $$-\overset{R_6}{\underset{|}{CH}}-O-\overset{O}{\underset{||}{C}}-R_7$$

wherein $R_6$ is hydrogen or lower alkyl and $R_7$ is lower alkyl.

$R_1$ represents hydrogen or methoxy. The $R_1$ substituent is in the α-configuration as indicated by the broken lines (≡).

A represents straight or branched chain alkylene of 1 to 6 carbons.

$R_2$ and $R_3$ are independently selected from hydrogen and straight chain alkyl of 1 to 4 carbons, or $R_2$ is hydrogen and $R_3$ is branched chain alkyl of 3 or 4 carbons, phenyl, benzyl or phenethyl, or $R_2$ and $R_3$ taken together with N atom to which they are attached form $$-N\diagup\diagdown\diagup\quad \text{or} \quad -N\diagup\diagdown\diagdown$$

$R_4$ represents hydrogen or lower alkyl.

$R_5$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

X represents hydrogen, lower alkanoyloxy, certain heterothio groups, $$-N\diagup\diagdown\diagup, \quad \text{or} \quad -N\diagup\diagdown\overset{O}{\underset{||}{C}}-NH_2.$$

When X is pyridinium or carbamoyl substituted pyridinium, the compounds can be structurally represented as having the formula $$R_5-\overset{H}{\underset{NH}{C^*}}-\overset{O}{\underset{}{C}}-\overset{R_1}{\underset{H}{N}}\underset{O}{\overset{S}{\underset{N}{\bigsqcup}}}\underset{COO^\ominus}{CH_2-N^\oplus}\diagup\diagdown Z \quad (Ia)$$
$$\overset{|}{C=O}$$
$$\overset{|}{N}-A-\overset{O}{\underset{||}{C}}-\overset{R_3}{\underset{|}{N}}$$
$$\overset{|}{R_4}\quad\quad R_2$$

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

Cycloalkyl refers to groups having 3 to 7 carbons in the ring, i.e. cyclopropyl, cyclobutyl, cyclopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or two substituents selected from halogen (preferably chlorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl, 2-, 3-, or 4-ethoxyphenyl, etc.

Straight or branch chain alkylene of 1 to 6 carbons is intended to include groups such as $-(CH_2)_n-$ wherein n is an integer from 1 to 6, $$-\underset{CH_3}{\overset{|}{CH}}-, \quad -\underset{CH_3}{\overset{CH_3}{\underset{|}{\overset{|}{C}}}}-, \quad -CH_2-\underset{CH_3}{\overset{|}{CH}}-,$$
$$-CH_2-\underset{CH_3}{\overset{|}{CH}}-CH_2-,$$

-continued $$-CH_2-CH(CH_3)-(CH_2)_2-, \text{ etc.}$$

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)silyl group.

The heterocyclic groups represented by $R_5$ are 2-thienyl, 3-thienyl, 2-furyl, 3-furyl, 2-pyridyl, 3-pyridyl, or 4-pyridyl. Also included within the meaning of $R_5$ are such heterocyclics having a halogen (preferably Cl or Br) or a lower alkyl of 1 to 4 carbons (preferably methyl or ethyl) substituent, i.e. 2-(4-chlorothienyl), 3-(4-methylthienyl), etc.

Lower alkanoyloxy refers to a group of the formula $$-O-\overset{O}{\underset{\|}{C}}-\text{lower alkyl}$$

wherein lower alkyl is of 1 to 4 carbons, preferably wherein lower alkyl is methyl.

The heterothio groups represented by X are

[structures of heterothio groups shown]

wherein $R_8$ is hydrogen or lower alkyl of 1 to 4 carbons (preferably methyl or ethyl) and $R_9$ is hydrogen, lower alkyl of 1 to 4 carbons (preferably methyl or ethyl), methoxy, hydroxy, or halogen (preferably chlorine).

The compounds of formula I wherein X is hydrogen, lower alkanoyloxy, or heterothio are prepared by reacting an α-amino intermediate of the formula

[structure II shown]  (II)

wherein X is hydrogen, lower alkanoyloxy, or heterothio, preferably in the form of its trifluoroacetic acid salt, with a compound of the formula $$R_2-\underset{R_3}{\underset{|}{N}}-\overset{O}{\underset{\|}{C}}-A-N=C=O \qquad \text{(III)}$$

or $$R_2-\underset{R_3}{\underset{|}{N}}-\overset{O}{\underset{\|}{C}}-A-\underset{R_4}{\underset{|}{N}}-\overset{O}{\underset{\|}{C}}-\text{halo} \qquad \text{(IV)}$$

or

[structure V shown]  (V)

wherein $R_2$, $R_3$, $R_4$ and A are as defined above and halo is Cl or Br.

The intermediates of formulas II to V are prepared by known methods. For example, the compounds of formula II can be prepared by various methods including the acylation of a 7-amino cephalosporin of the formula

[structure VI shown]  (VI)

with a substituted α-amino acid of the formula $$R_5-\underset{NH-Y}{\underset{|}{CH}}-COOH \qquad \text{(VII)}$$

wherein Y is a protecting group such as

[structures of protecting groups shown]

-continued $$(CH_3)_3-C-O-\overset{O}{\underset{\|}{C}}-.$$

The α-amino protecting group is then removed by treating the resulting cephalosporin with trifluoroacetic acid and anisole. The desmethoxy α-amino compounds of formula II are taught in various U.S. patents as for example, U.S. Pat. Nos. 3,485,819; 3,507,861; 3,641,021; 3,796,801; 3,813,388; 3,821,207; etc. Similarly, the 7α-methoxy compounds of formula II prepared by various means are disclosed in U.S. patents as for example, U.S. Pat. Nos. 3,775,410; 3,780,031; 3,780,033; 3,780,034; 3,780,037; 3,887,549; etc. Also, the 7α-methoxy-7-amino compounds of formula VI are taught in U.S. Pat. No. 3,897,424.

Alternatively, the compounds of formula I wherein X is hydrogen, lower alkanoyloxy, or heterothio can be prepared by reacting a compound of the formula $$R_5-\overset{H}{\underset{|}{\overset{|}{\underset{NH}{C^*}}}}-\overset{O}{\underset{\|}{C}}-O-\underset{}{\bigcirc}-NO_2 \quad (VIII)$$
$$\underset{|}{\overset{|}{C=O}}$$
$$N-A-\overset{O}{\underset{\|}{C}}-N-R_3$$
$$\underset{R_4}{|} \quad \underset{R_2}{|}$$

wherein $R_2$, $R_3$, $R_4$, $R_5$ and A are as defined above, with an ester, preferably R is diphenylmethyl, of the compound of formula VI.

The intermediate of formula VIII can be prepared by reacting the isocyanatoacetic acid ester of the formula $$R_5-\overset{H}{\underset{|}{\overset{|}{\underset{NCO}{C^*}}}}-\overset{O}{\underset{\|}{C}}-O-\underset{}{\bigcirc}-NO_2 \quad (IX)$$

with the compound of the formula $$R_2-\overset{}{\underset{|}{N}}-\overset{O}{\underset{\|}{C}}-A-\overset{}{\underset{|}{N}}-H. \quad (X)$$
$$\underset{R_3}{} \quad \underset{R_4}{}$$

The compounds of formula Ia are prepared by reacting the compound of the formula (or its sodium salt)

$$R_5-\overset{H}{\underset{|}{\overset{|}{\underset{NH}{C^*}}}}-\overset{O}{\underset{\|}{C}}-N\overset{R_1}{\underset{H}{\equiv}}\underset{N}{\overset{S}{\diagup}}\underset{COOH}{\diagdown}CH_2OCCH_3 \quad (Ib)$$
$$\underset{|}{\overset{|}{C=O}} \quad O$$
$$N-A-\overset{}{\underset{\|}{C}}-N-R_3$$
$$\underset{R_4}{|} \quad \overset{O}{\underset{R_2}{|}}$$

with pyridine or carbamoyl substituted pyridine in a polar solvent such as water and in the presence of a catalyst such as an alkali metal thiocyanate. U.S. Pat. No. 3,792,047 and German Offenlegungsschrift No. 2,234,280 both disclose methods for reacting a cephalosporin so as to replace an acetoxy group with a pyridinium group.

Also, the compounds of formula I wherein $R_1$ is either hydrogen or methoxy and X is heterothio can be prepared by reacting the compound of formula Ib with a mercaptan of the formula $$\text{hetero}-S-H \quad (XI)$$

or an alkali metal (preferably sodium) mercaptan salt of the formula $$\text{hetero}-S-\text{alkali metal}. \quad (XII)$$

Methods for displacing the acetoxy group of a cephalosporin by a heterothio group are taught in various U.S. patents including U.S. Pat. Nos. 3,855,213; 3,890,309; 3,892,737; etc.

The compounds of formula I wherein R is lower alkyl, phenyl-lower alkyl, trihaloethyl, diphenyl-lower alkyl, or the acyloxymethyl group $$-\overset{R_6}{\underset{|}{C}}H-O-\overset{O}{\underset{\|}{C}}-R_7$$

may be obtained by reacting the 7-amino cephalosporin of formula VI either before or after the acylation of the 7-amino substituent with one or two moles of a compound of the formula $$\text{halo}-R \quad (XIII)$$

or $$R=N^+|N^- \quad (XIV)$$

wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compound of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention. Also, a second asymmetric carbon atom can be present in the alkylene chain, for example $$-\overset{H}{\underset{|}{\overset{|}{\underset{CH_3}{C^*}}}}-\overset{O}{\underset{\|}{C}}-N-R_3.$$
$$\underset{R_2}{|}$$

Preferred compounds of this invention are those wherein R is hydrogen or an alkali metal ion; X is pyridinium, carbamoyl substituted pyridinium (particularly where the carbamoyl group is in the 4-position), or heterothio; $R_5$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl, or ethyl; $R_2$ and $R_3$ are independently selected from hydrogen and straight chain alkyl of 1 to 4 carbons, or $R_2$ is hydrogen and $R_3$ is branched alkyl of 3 or 4 carbons, phenyl, benzyl or phenethyl, or $R_2$ and $R_3$ taken together with N atom to which they are attached form

or

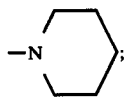

A is straight or branched chain alkylene of 1 to 4 carbons; and $R_4$ is hydrogen or straight or branched chain alkyl of 1 to 4 carbons.

Also preferred as both final products and intermediates are the compounds of formula I wherein X is

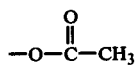

and A, R, $R_2$, $R_3$ and $R_4$ are as defined above.

The most preferred final compounds are those of formula I wherein R is hydrogen or an alkali metal ion; $R_5$ is 2-thienyl, 3-thienyl, phenyl, or 4-hydroxyphenyl, particularly, 2-thienyl; $R_2$ and $R_3$ are independently selected from hydrogen, methyl, and ethyl, particularly wherein $R_2$ and $R_3$ are both hydrogen; $R_4$ is hydrogen or methyl, particularly hydrogen; A is straight or branched chain alkylene of 1 to 4 carbons, especially —$(CH_2)_2$—; and X is heterothio, particularly wherein X is

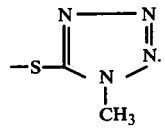

The compounds of formula I wherein R is hydrogen have a broad spectrum of antibacterial activity against both gram positive and gram negative organisms such as *Staphylococcus aureus, Salmonella schottmuelleri, Proteus rettgeri, Escherichia coli, Enterobacter hafniae, Enterobacter cloacae, Klebsiella pneumoniae, Serratia marcescens,* etc. They may be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg. of body weight, daily, orally or parenterally, in single or two to four divided doses to treat infections of bacterial origin, e.g., 5.0 mg./kg. in mice.

Up to about 600 mg. of a compound of formula I wherein R is hydrogen or a physiologically acceptable salt thereof may be incorporated in an oral dosage form such as tablets, capsules or elixirs or in an injectable form in a sterile aqueous vehicle prepared according to conventional pharmaceutical practice.

Illustrative process details are provided in the examples for the various reactions. All temperatures are on the centigrade scale.

EXAMPLE 1

7β-[[D-[[[(2-Amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid (a) D-α-[[[(4-Methoxyphenyl)methoxy]carbonyl]amino]-2-thiopheneacetic acid 74 g. of D-2-Thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-α-[[[(4-methoxyphenyl)methoxy]carbonyl]amino]-2-thiopheneacetic acid; m.p. 84°–94° [α]$_{20}^D$: −69° (c=1, tetrahydrofuran).

(b) D-α-[[[(4-Methoxyphenyl)methoxy]carbonyl]amino]-2-thiopheneacetic acid, 4-nitrophenyl ester 64.8 g. (0.2 mole) of D-α-[[[(4-methoxyphenyl)methoxy]carbonyl]amino]-2-thiopheneacetic acid from part (a) are dissolved in 330 ml. of anhydrous tetrahydrofuran. A solution of 28 g. (0.2 mole) of 4-nitrophenol in 330 ml. of tetrahydrofuran is added. The mixture is cooled to 0° and a solution of 41.4 g. (0.2 mol) of dicyclohexylcarbodiimide in 134 ml. of tetrahydrofuran is added dropwise over a period of 90 minutes. The mixture is stirred overnight at 0°. It is then filtered and the filtrate is concentrated to yield 90 g. of crude product. Crystallization from toluene yields D-α-[[[(4-methoxyphenyl)methoxy]carbonyl]amino]-2-thiopheneacetic acid, 4-nitrophenyl ester; m.p. 98°–105° (dec.).

(c) D-α-Amino-2-thiopheneacetic acid, 4-nitrophenyl ester, hydrochloride 63.8 g. of D-α-[[[(4-methoxyphenyl)methoxy]carbonyl]amino]-2-thiopheneactic acid, 4-nitrophenyl ester from part (b) are added at 0° to 300 ml. of a saturated solution of HCl gas in glacial acetic acid. The nitrophenyl ester from part (b) goes into solution and shortly thereafter the hydrochloride salt precipitates as a thick crystalline slurry. The hydrochloride salt is filtered under suction and additional hydrochloride salt is obtained from the filtrate by concentrating to give a combined yield of 46.2 g. of D-α-amino-2-thiopheneacetic acid, 4-nitrophenyl ester, hydrochloride; m.p. 173°–176° (dec.).

(d) D-α-Isocyanato-2-thiopheneacetic acid, 4-nitrophenyl ester

Phosgene is passed into a boiling suspension of 21 g. of D-2-amino-2-thiopheneacetic acid, 4-nitrophenyl ester, hydrochloride in 300 ml. of toluene until a clear solution results. After concentrating, D-α-isocyanato-2-thiopheneacetic acid, 4-nitrophenyl ester remains as an oil residue.

(e)
D-α-[[[(2-Amino-2-oxoethyl)amino]carbonyl]amino]-2-thiopheneacetic acid, 4-nitrophenyl ester 1.4 g. of glycinamide (produced from the hydrochloride salt by treatment with sodium methoxide in methanol) are dissolved in 100 ml. of absolute chloroform and 6 g. of D-α-isocyanato-2-thiopheneacetic acid, 4-nitro phenyl ester from part (d) dissolved in 50 ml. of absolute chloroform are added dropwise at room temperature. After stirring for 1 hour a thick yellow slurry forms. The precipitate is collected and dried (5.5 g. crude product). The product is purified by dissolving in 50 ml. of dimethylformamide, 250 ml. of dioxane are added and the mixture is treated with charcoal and filtered. After the addition of 50 ml. of petroleum ether the product, D-α-[[[(2-amino-2-oxoethyl)amino]carbonyl]amino]-2-thiopheneacetic acid, 4-nitrophenyl ester, comes out as a gel-like precipitate, yield 2.7 g., m.p. 165°–168°.

(f)
7β-[[D-[[[(2-Amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 1.89 g. of the product from part (e) together with 1.5 g. of 1-hydroxybenzotriazole and 2.5 g. of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester are dissolved in 30 ml. of dimethylacetamide and stirred at room temperature for four hours. The reaction mixture is added to 300 ml. of water and this mixture is extracted three times with 100 ml. portions of ethyl acetate. The organic phase is extracted first with 200 ml. of water, then with 100 ml. of 5% sodium bicarbonate solution and again with 100 ml. of water, then dried over a sodium sulfate. On concentrating the ethyl acetate solution, the product, 7β-[[D-[[[(2-amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester crystallizes, biege crystals, m.p. 122°–126°. The product is reprecipitated from tetrahydrofuran-ether, yield 2.3 g.

(g)
7β-[[D-[[[(2-Amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 2.3 g. of the diphenylmethyl ester product from part (f) are treated with 30 ml. of trifluoroacetic acid and anisole (4:1) for 10 minutes at −10°. Concentrating in a rotary evaporator and treating with absolute ether yields 1.3 g. of crude product. The crude product is purified by dissolving in 80 ml. of isopropanol while warming, filtering, and precipitating the ether-petroleum ether to yield 0.5 g. of 7β-[[D-[[[(2-amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, as a biege powder; m.p. 152°–157°.

An aqueous equimolar solution of this acid and potassium bicarbonate is lyophilized to yield 7β-[[D-[[[(2-amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt; m.p. 163°–171° (dec.). By substituting sodium bicarbonate for the potassium bicarbonate, one obtains the corresponding sodium salt.

EXAMPLE 2

7β-[[L-[[[(2-Amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid Following the procedure of example 1 but substituting L-thienylglycine for the D-thienylglycine in part (a), one obtains 7β-[[L-[[[(2-amino-2-oxoethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid and its potassium or sodium salt.

EXAMPLES 3–46

Following the procedure of example 1 but employing the amide shown below in Col. II and the isocyanato acetic acid ester shown in Col. I one obtains the intermediate shown in Col. III. This intermediate is then reacted with the cephalosporanic acid ester shown in Col. IV and after removal of the ester protecting group yields the compound shown in Col. V.

| Col. I | Col. II |
|---|---|
| 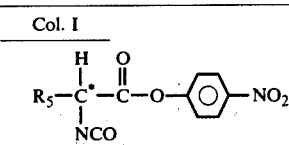 | 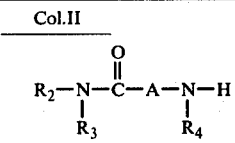 |

-continued

| Col. III | Col. IV |
|---|---|
| R5-C*H(NH-C(=O)-N(R4)-A-C(=O)-N(R2)(R3))-C(=O)-O-C6H4-NO2 | H2N-C(R1)H-[β-lactam-cephem]-CH2X, COOCH(C6H5)2 |

Col. V

R5-C*H(NH-C(=O)-N(R4)-A-C(=O)-N(R2)(R3))-C(=O)-NH-C(R1)H-[β-lactam-cephem]-CH2X, COOH

| Ex. | R5 | R2 | R3 | R4 | A | R1 | X |
|---|---|---|---|---|---|---|---|
| 3 | 2-thienyl | —H | —H | —H | —CH2— | —OCH3 | —S-(1-methyl-tetrazol-5-yl) |
| 4 | 2-thienyl | —H | —H | —H | —(CH2)2— | H | —S-(5-methyl-1,3,4-thiadiazol-2-yl) |
| 5 | 5-chloro-2-thienyl | —H | —H | —H | —C(CH3)2— | H | —S-(5-methyl-1,3,4-oxadiazol-2-yl) |
| 6 | 3-methyl-2-thienyl | —H | —H | —H | —CH2— | —OCH3 | —S-(5-ethyl-1,3,4-thiadiazol-2-yl) |
| 7 | 2-furyl | —H | —H | —H | —CH(CH3)—CH2— | —H | —S-(1-methyl-tetrazol-5-yl) |
| 8 | 5-methyl-2-furyl | —H | —H | —H | —(CH2)4— | —OCH3 | —S-(5-ethyl-1,3,4-thiadiazol-2-yl) |
| 9 | 4-bromo-2-furyl | —H | —H | —H | —(CH2)6— | —H | —S-(1H-1,2,3-triazol-5-yl) |
| 10 | 2-thienyl | —CH3 | —CH3 | —H | —CH2— | —H | —O-C(=O)-CH3 |
| 11 | 2-furyl | —C2H5 | —C2H5 | —H | —CH2-C(CH3)2-CH2— | —H | —H |
| 12 | 2-pyridyl | —H | —H | —H | —(CH2)3— | —OCH3 | —S-(1,3,4-thiadiazol with fused tetrazole) |

-continued
| | | | | | | | |
|---|---|---|---|---|---|---|---|
| 13 | 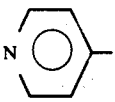 | —H | —H | —H | —CH$_2$—CH—CH$_2$—<br>　　　　CH$_3$ | —H | 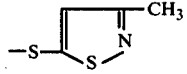 |
| 14 | 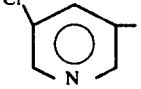 | —H | —H | —H | —(CH$_2$)$_5$— | —H | 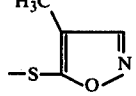 |
| 15 |  | —H | —H | —H | —CH$_2$— | —H | 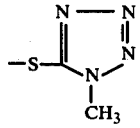 |
| 16 | 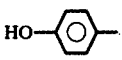 | —H | —H | —H | —CH$_2$— | —H | 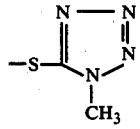 |
| 17 |  | —H | —H | —H | —(CH$_2$)$_2$— | —OCH$_3$ | 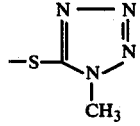 |
| 18 | 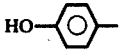 | —CH$_3$ | —CH$_3$ | —H | —(CH$_2$)$_3$— | —OCH$_3$ | 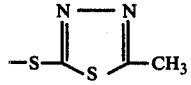 |
| 19 | 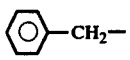 | —H | —H | —H | —CH—CH$_2$—<br>　C$_2$H$_5$ | —H | 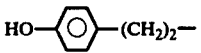 |
| 20 | 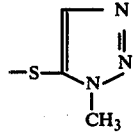 | —H | —H | —H | —(CH$_2$)$_2$— | —H | 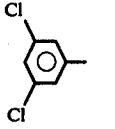 |
| 21 | 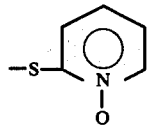 | —H | —H | —H | —CH$_2$— | —OCH$_3$ | 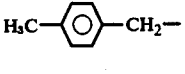 |
| 22 | 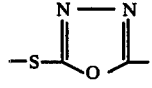 | —H | —H | —H | 　　CH$_3$<br>—C—CH$_2$—<br>　　CH$_3$ | —H | 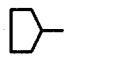 |
| 23 | 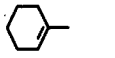 | —H | —H | —H | —(CH$_2$)$_5$— | —H | 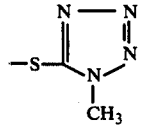 |
| 24 |  | —H | —H | —H | 　　　CH$_3$<br>—CH$_2$—C—<br>　　　CH$_3$ | —H | 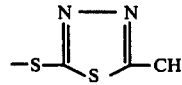 |
| 25 |  | —H | —H | —H | —CH$_2$— | —OCH$_3$ | |

| | | | | | | | |
|---|---|---|---|---|---|---|---|
| 26 | phenyl | —H | —H | —H | —(CH$_2$)$_2$— | —H | 1-methyl-tetrazol-5-ylthio |
| 27 | phenyl | —H | —H | —H | —CH$_2$— | —OCH$_3$ | —H |
| 28 | H— | —H | —H | —H | —CH$_2$— | —H | 5-methyl-1,3,4-oxadiazol-2-ylthio |
| 29 | C$_2$H$_5$— | —H | —H | —H | —(CH$_2$)$_2$— | —H | —O—C(=O)—C$_3$H$_7$ |
| 30 | 2-thienyl | —C$_2$H$_5$ | —C$_2$H$_5$ | —H | —C(CH$_3$)$_2$—CH$_2$— | —OCH$_3$ | 1-ethyl-tetrazol-5-ylthio |
| 31 | 2-thienyl | —H | i-C$_3$H$_7$ | —H | —CH$_2$— | —H | 1,3,4-thiadiazol-2-ylthio |
| 32 | 3-methyl-2-thienyl | —H | n-C$_4$H$_9$ | —H | —(CH$_2$)$_2$— | —H | —O—C(=O)—CH$_3$ |
| 33 | phenyl | —H | t-C$_4$H$_9$ | —H | —CH$_2$—C(CH$_3$)$_2$—CH$_2$— | —OCH$_3$ | tetrazol-5-ylthio (NH) |
| 34 | 4-hydroxyphenyl | —H | phenyl | —H | —CH$_2$— | —H | 1,3,4-thiadiazol-2-ylthio |
| 35 | 4-bromobenzyl | —H | —CH$_2$-phenyl | —H | —CH$_2$— | —OCH$_3$ | 5-ethyl-1,3,4-oxadiazol-2-ylthio |
| 36 | 4-methoxyphenyl | —H | —(CH$_2$)$_2$-phenyl | —H | —CH$_2$— | —H | 5-methyl-1,3,4-thiadiazol-2-ylthio |
| 37 | 2-thienyl | —H | —H | —CH$_3$ | —CH$_2$— | —H | 1-methyl-tetrazol-5-ylthio |
| 38 | 2-thienyl | —CH$_3$ | —CH$_3$ | —CH$_3$ | —(CH$_2$)$_2$— | —OCH$_3$ | 5-methyl-1,3,4-thiadiazol-2-ylthio |
| 39 | phenyl | —H | —H | —C$_2$H$_5$ | —CH$_2$— | —H | 1-methyl-tetrazol-5-ylthio |
| 40 | phenyl | —H | —CH$_3$ | —CH$_3$ | —C(CH$_3$)$_2$—CH$_2$— | —OCH$_3$ | —O—C(=O)—CH$_3$ |

-continued

| # | Col I | Col II | Col III | Col IV | Col V | Col VI |
|---|---|---|---|---|---|---|
| 41 | HO—⌬— | —H | —H | -i-C$_3$H$_7$ | —CH$_2$— | —H | —S—(thiadiazole-CH$_3$) |
| 42 | (thienyl) | —N(pyrrolidino) | —H | —CH$_2$— | —H | —S—(N-methyltetrazole) |
| 43 | (thienyl) | —N(piperidino) | —CH$_3$ | —(CH$_2$)$_4$— | —H | —S—(thiadiazole-CH$_3$) |
| 44 | (thienyl) | —N(piperidino) | —CH$_3$ | —C(CH$_3$)$_2$— | —OCH$_3$ | —S—(N-methyltetrazole) |
| 45 | (phenyl) | —N(pyrrolidino) | —H | —CH$_2$— | —OCH$_3$ | —S—(N-methyltetrazole) |
| 46 | (phenyl) | —N(piperidino) | —C$_2$H$_5$ | —CH$_2$—CH(CH$_3$)— | —H | —S—(N-methyltetrazole) |

The final products of Col. V can be reacted so as to obtain the corresponding salts or esters according to methods known in the art. The final compound can be obtained as the D-isomer, L-isomer, or the D,L-isomeric mixture depending upon the configuration of the starting material of Col. I.

EXAMPLE 47

7β-[[D-[[[(2-Amino-2-oxoethyl)amino]carbonyl-]amino]-2-thienylacetyl]amino]-3-[[4-(aminocarbonyl)-pyridino]methyl]-8-oxo-5-thia-1-azabicyclo[4.2.0]oct-2-ene-2-carboxylic acid, sodium salt

(a)

3-[(Acetyloxy)methyl]-7β-[[D-[[[(4-methoxyphenyl)-methoxy]carbonyl]amino]-2-thienylacetyl]amino]-8-oxo-5-thia-1-azabicyclo[4.2.0]oct-2-ene-2-carboxylic acid 3.2 g. (0.01 mole) of the D-α-[[[(4-methoxyphenyl)-methoxy]carbonyl]amino]-2-thiopheneacetic acid from example 1(a) are brought into solution in 40 ml. of methylene chloride with 1.1 ml. of N-methylmorpholine. The solution is cooled to −15°, 1.39 ml. of isobutyl-chloroformate are added, and the mixture is stirred for 10 minutes. To this is added a solution of 3.26 g. (0.1012 mol.) of 7-aminocephalosporanic acid and 3.1 ml. of triethylamine in 40 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration, 2 g. of 3-[(acetyloxy)methyl]-7β-[[D-[[[(4-methoxyphenyl)methoxy]carbonyl]amino]-2-thienylacetyl]amino]-8-oxo-5-thia-1-azabicyclo[4.2.-0]oct-2-ene-2-carboxylic acid, crystallize; m.p. 142°-143° (dec.).

(b)

3-[(Acetyloxy)methyl]-7β-[D-2-amino-2-(2-thienyl)acetamido]-8-oxo-5-thia-1-azabicyclo[4.2.0]oct-2-ene-2-carboxylic acid, trifluoroacetic acid salt (1:1)

2.0 g. of the product from part (a) are added at −5° to a mixture of 10 ml. of trifluoroacetic acid and 4 ml. of anisole. The mixture is stirred for 10 minutes and is then concentrated in a rotary evaporator. The residue is treated with ether and filtered to yield the titled compound.

(c)

3-[(Acetyloxy)methyl]-7β-[[D-[[[(2-amino-2-oxoethyl)amino]carbonyl]amino]-2-thienylacetyl]amino]-8-oxo-5-thia-1-azabicyclo[4.2.0]oct-2-ene-2-carboxylic acid, sodium salt The trifluoroacetic acid salt product of part (b) is suspended in methylene chloride and reacted with a slight molar excess of (2-amino-2-oxoethyl)carbamic chloride to yield after separation 3-[(acetyloxy)methyl]-7β-[[D-[[[(2-amino-2-oxoethyl)amino]carbonyl]amino]-2-thienylacetyl]amino]-8-oxo-5-thia-1-azabicyclo-[4.2.0]oct-2-ene-2-carboxylic acid.

An equimolar aqueous solution of this acid and sodium bicarbonate is lyophilized to yield as a powder 3-[(acetyloxy)methyl]-7β-[[D-[[[(2amino-2-oxoethyl)amino]carbonyl]amino]-2-thienylacetyl]amino]-8-oxo- 5-thia-1-azabicyclo[4.2.0]oct-2-ene-2-carboxylic acid, sodium salt.

(d)

7β-[[D-[[[(2-Amino-2-oxoethyl)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid, sodium salt

A mixture of 0.005 mole of the sodium salt product of part (c), 0.0075 mole of 4-pyridinecarboxamide, 12 g. of potassium thiocyanate and 7.5 ml. of water are heated at 50° for 24 hours. The clear solution is passed through a chromatography column filled with 150 g. of ion exchanger Amberlite XAD-2. The column is eluted with water and all fractions in which the desired product is shown by thin layer chromatography are combined. The combined fractions are lyophilized. The amorphous residue is triturated with ether and filtered under suction to yield 7β-[[D-[[[(2-amino-2oxoethyl)amino]-carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid, sodium salt.

Similarly, by employing L-α-[[[(4-methoxyphenyl)-methoxy]carbonyl]amino]-2-thiopheneacetic acid in place of the D-isomer in the above procedure, one obtains 7β-[[L-[[[(2-amino-2-oxoethyl)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid, sodium salt.

EXAMPLES 48-68

Following the procedure of example 47 but employing the cephalosporanic acid trifluoroacetic acid salt shown in Col. I and either the carbamic chloride shown in Col. II or the isocyanate compound shown in Col. III (when R₄ is other than hydrogen the carbamic chloride is employed) one obtains the sodium salt shown in Col. IV. This compound is then reacted with the pyridine compound shown in Col. V to yield the product shown in Col. VI.

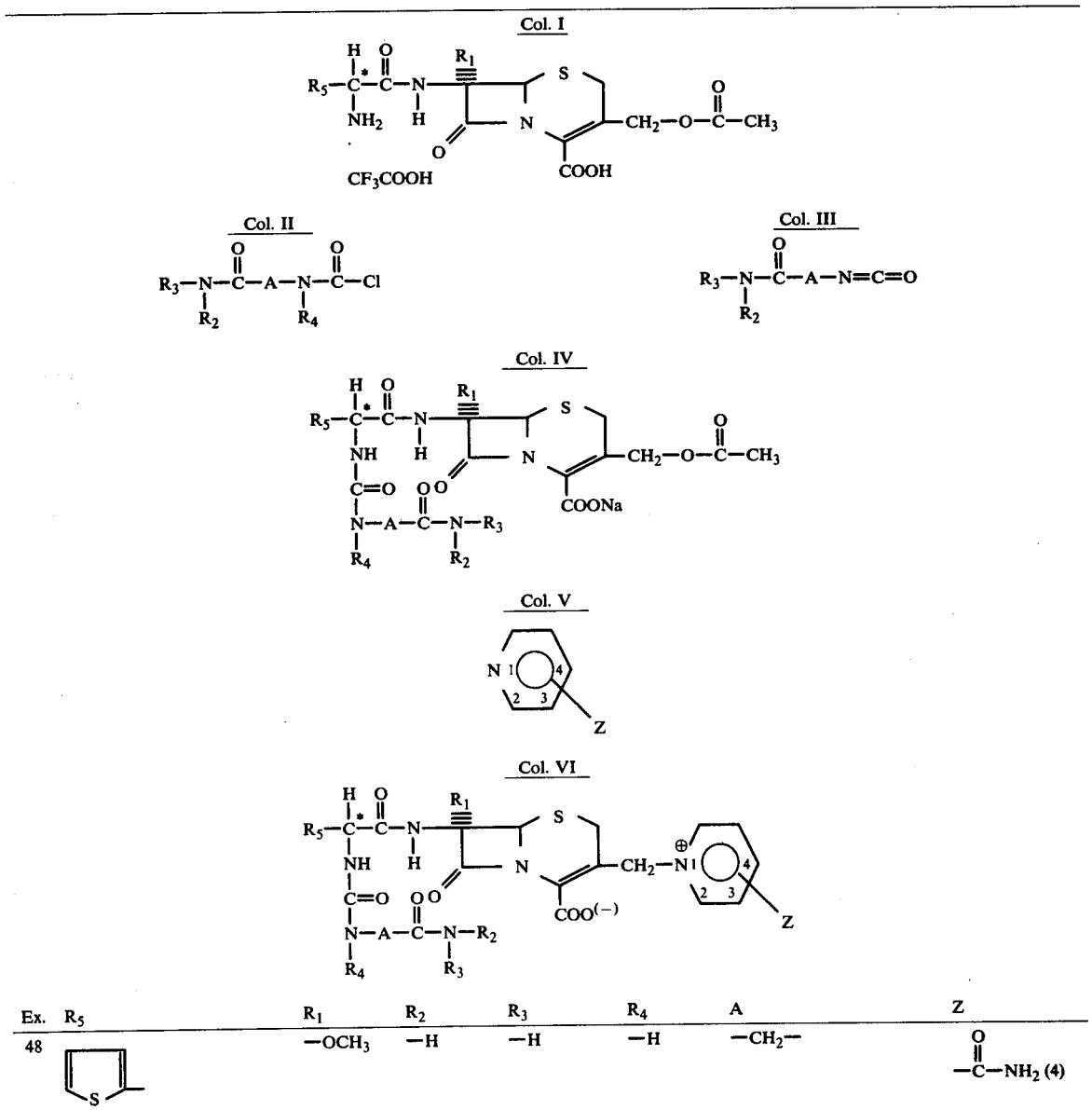

| Ex. | $R_5$ | $R_1$ | $R_2$ | $R_3$ | $R_4$ | A | Z |
|---|---|---|---|---|---|---|---|
| 48 | (thienyl) | —OCH₃ | —H | —H | —H | —CH₂— | —C(=O)—NH₂ (4) |

-continued

| No. | Ring | R1 | R2 | R3 | R4 | Linker | Terminal |
|---|---|---|---|---|---|---|---|
| 49 | 2-chlorothien-5-yl | —H | —CH₃ | —CH₃ | —H | —(CH₂)₂— | —C(=O)—NH₂ (4) |
| 50 | furan-2-yl | —OCH₃ | —H | —C₂H₅ | —H | —C(CH₃)₂—CH₂— | —C(=O)—NH₂ (3) |
| 51 | furan-2-yl | —H | —H | —t-C₄H₉ | —H | —(CH₂)₄— | —H |
| 52 | pyridin-2-yl | —OCH₃ | —C₂H₅ | —CH₃ | —CH₃ | —CH₂— | —C(=O)—NH₂ (2) |
| 53 | pyridin-4-yl | —H | —H | —CH₂— | —H | —(CH₂)₆— | —C(=O)—NH₂ (4) |
| 54 | phenyl | —H | —H | —H | —H | —CH₂— | —C(=O)—NH₂ (4) |
| 55 | phenyl | —OCH₃ | —H | —H | —H | —CH₂— | —C(=O)—NH₂ (4) |
| 56 | 4-hydroxyphenyl | —H | —CH₃ | —CH₃ | —H | —CH₂— | —C(=O)—NH₂ (4) |
| 57 | 4-hydroxyphenyl | —OCH₃ | —H | —H | —CH₃ | —CH₂— | —H |
| 58 | 4-chlorophenyl | —H | —H | phenyl | —CH₃ | —CH₂—CH(CH₃)—CH₂— | —C(=O)—NH₂ (4) |
| 59 | 4-methylbenzyl | —OCH₃ | —H | —C₂H₅ | —C₂H₅ | —CH₂— | —H |
| 60 | cyclohexyl | —H | —H | —H | —H | —C(CH₃)₂—CH₂— | —C(=O)—NH₂ (2) |
| 61 | cyclohexen-1-yl | —OCH₃ | —H | —H | —H | —CH₂— | —H |
| 62 | thien-2-yl | —H | —H | pyrrolidin-1-yl | —H | —CH₂— | —C(=O)—NH₂ (4) |
| 63 | 5-methylthien-2-yl | —OCH₃ | —H | piperidin-1-yl | —H | —(CH₂)₂— | —C(=O)—NH₂ (4) |

| | | | | | |
|---|---|---|---|---|---|
| 64 | 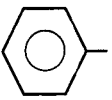 —H |  | —CH₃ | —CH₂— | —H |
| 65 | 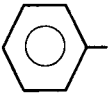 —OCH₃ | 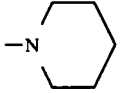 | —H | —(CH₂)₂— | $-\overset{\underset{\parallel}{O}}{C}-NH_2$ (3) |
| 66 | 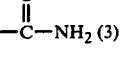 —OCH₃ | 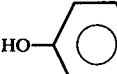 | —C₂H₅ | —CH₂— | —H |
| 67 | 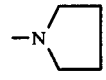 —H | 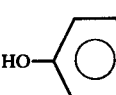 | —H | $-\overset{\underset{CH_3}{\mid}}{\underset{\mid}{C}}-CH_2-$ $CH_3$ | $-\overset{\underset{\parallel}{O}}{C}-NH_2$ (4) |
| 68 | 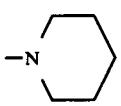 —H | 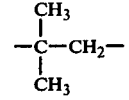 | —H | —(CH₂)₄— | $-\overset{\underset{\parallel}{O}}{C}-NH_2$ (4) |

The final compounds can be obtained in the D-, L-, or D,L-isomeric form.

EXAMPLE 69

7β-[[D-[[[(2-Amino-2-oxoethyl)amino]carbonyl]amino]-2-thienylacetyl]amino]-3-[[(1-oxo-2-pyridinyl)thio]methyl]-8-oxo-5-thia-1-azabicyclo[4.2.0]oct-2-ene-2-carboxylic acid 0.003 mole of 3-[(acetyloxy)methyl]-7β-[[D-[[[(2-amino-2-oxoethyl)amino]carbonyl]amino]-2-thienylacetyl]amino]-8-oxo-5-thia-1-azabicyclo[4.2.-0]oct-2-ene-2-carboxylic acid, sodium salt from example 47(c) and 0.004 mole of 2-mercaptopyridine, 1-oxide sodium salt are dissolved in 15 ml. of water and heated overnight at 50°. The reaction mixture is then diluted with water, filtered, and the clear solution is adjusted to a pH of 2 by the addition of 2N hydrochloric acid. The resulting precipitate is filtered under suction to obtain 7β-[[D-[[[(2-amino-2-oxoethyl)amino]carbonyl]amino]-2-thienylacetyl]amino]-3-[[(1-oxo-2-pyridinyl)thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(2-amino-2-oxoethyl)amino]carbonyl]amino]-2-thienylacetyl]amino]-8-oxo-5-thia-1-azabicyclo[4.2.0]oct-2-ene-2-carboxylic acid, sodium salt, one obtains the corresponding final product in the L-form.

Similarly, the various 3-[(acetyloxy)methyl]-7α-methoxy or desmethoxy-7β-acylureido-cephalosporanic acid sodium salts of Col. IV of examples 48 to 68 may be employed in the procedure of example 69 to obtain other 3-[[(1-oxo-2-pyridinyl)thio]methyl]cephalosporins within the scope of the invention.

EXAMPLE 70

7β-[[D-[[[(2-Amino-2-oxoethyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid 3-[(Acetyloxy)methyl]-7β-[[D-[[[(2-amino-2-oxoethyl)amino]carbonyl]amino]-2-thienylacetyl]amino]-8-oxo-5-thia-1-azabicyclo[4.2.0]oct-2-ene-2-carboxylic acid, sodium salt from example 47(c) is dissolved in a mixture of acetone:water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 7β-[[D-[[[(2-amino-2-oxoethyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(2-amino-2-oxoethyl)amino]carbonyl]amino]-2-thienylacetyl]amino]-8-oxo-5-thia-1-azabicyclo[4.2.0]oct-2-ene-2-carboxylic acid, sodium salt, one obtains the corresponding final product in the L- form.

EXAMPLES 71–79

Following the procedure of example 70 but substituting for the 1-oxopyridazine-3-thiol one of the following:
2-oxopyridazine-3-thiol
6-methyl-1-oxopyridazine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol
one obtains:

7β-[[D-[[[(2-amino-2-oxoethyl)amino]carbonyl]amino]-2-thienylacetyl]amino]-3-[[(2-oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-methyl-1-oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-methoxy-1- oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-t-butyl-2-oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-ethyl-2-oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-hydroxy-1-oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-hydroxy-2-oxopyridazin-3-yl)thio]methyl]-8-oxo-5-thia-1-azabicyclo[4.2.0]oct-2-ene-2-carboxylic acid, 7β-[[D-[[[(2-amino-2-oxoethyl)amino]carbonyl]amino]-2-thienylacetyl]amino]-3-[[(6-chloro-1-oxopyridazin-3-yl)thio]methyl]-8-oxo-5-thia-1-azabicyclo[4.2.0]oct-2-ene-2-carboxylic acid, and 7β-[[D-[[[(2-amino-2-oxoethyl)amino]carbonyl]amino]-2-thienylacetyl]amino]-3-[[(6-chloro-2-oxopyridazin-3-yl)thio]methyl]-8-oxo-5-thia-1-azabicyclo[4.2.0]oct-2-ene-2-carboxylic acid, respectively.

Similarly, by employing 3-[(acetyloxy)methyl]-7β-[[L-[[[(2-amino-2-oxoethyl)amino]carbonyl]amino]-2-thienylacetyl]amino]-8-oxo-5-thia-1-azabicyclo[4.2.0]oct-2-ene-2-carboxylic acid, sodium salt in place of the D-isomer in examples 70 to 79, the corresponding final products in the L-isomer form are obtained. Additionally, the various 3-[(acetyloxy)methyl]-7α-methoxy or desmethoxy-7β-acylureido-cephalosporanic acid sodium salts shown in Col. IV of examples 48 to 68 may be employed in the procedure of examples 70 to 79 to obtain other compounds with the scope of the invention.

EXAMPLES 80–90

Following the procedure of example 70 but employing the 3-[(acetyloxy)methyl]-7α-methoxy or desmethoxy-7-acylureido-cephalosporin sodium salt of Col. I and the heteromercapto of Col. II, one obtains the 3-heterothio compounds of Col. III.

Col. I

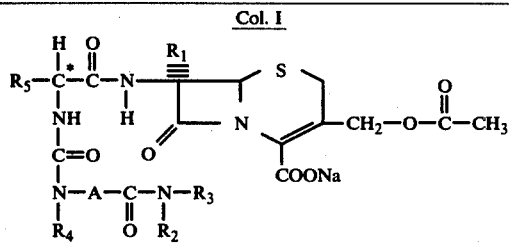

Col. II hetero-S—H

Col. III

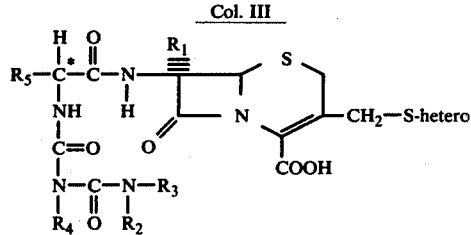

| Ex. | $R_5$ | $R_1$ | $R_2$ | $R_3$ | $R_4$ | A | hetero |
|---|---|---|---|---|---|---|---|
| 80 | thienyl | —OCH₃ | —H | —H | —CH₃ | —CH₂— | N-methyl-triazole |
| 81 | 5-methyl-furyl | —H | —CH₃ | —CH₃ | —H | —(CH₂)₄— | 2-ethyl-thiadiazole |
| 82 | pyridyl | —H | —H | —H | —H | —C(CH₃)₂— | 3-methyl-isoxazole |
| 83 | phenyl | —OCH₃ | —H | —H | —H | —C(CH₃)₂CH₂— | 3-ethyl-isothiazole |

The final products can be obtained in the D-, L-, or D,L-isomeric form.

What is claimed is:

1. A compound of the formula:

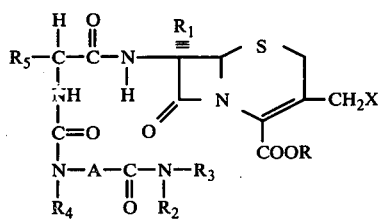

wherein R is hydrogen, lower alkyl, phenyl-lower alkyl, diphenyl-lower alkyl, tri(lower alkyl)silyl, trihaloethyl, an alkali metal ion, an alkaline earth metal ion, dibenzylamine, N,N-dibenzylethylenediamine, methylamine, triethylamine, N-ethylpiperidine, or

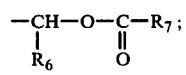

$R_1$ is in the α-configuration and is hydrogen or methoxy; $R_2$ and $R_3$ are independently selected from hydrogen and straight chain alkyl of 1 to 4 carbons, or $R_2$ is hydrogen and $R_3$ is branched chain alkyl of 3 to 4 carbons, phenyl, benzyl or phenethyl, or $R_2$ and $R_3$ taken together with the N atom to which they are attached form

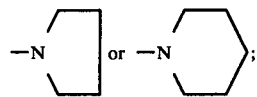

$R_4$ is hydrogen or lower alkyl; A is straight or branched chain alkylene of 1 to 6 carbons; $R_5$ is hydrogen, lower alkyl, cycloalkyl of 3 to 7 carbons, cycloalkenyl of 3 to 7 carbons, cycloalkadienyl of 6 to 7 carbons, phenyl, phenyl-lower alkyl, substituted phenyl or phenyl-lower alkyl wherein said phenyl substituent is one or two members selected from the group consisting of halogen, lower alkyl of 1 to 4 carbons, lower alkoxy of 1 to 4 carbons, and hydroxy, or a mono-substituted or unsubstituted heterocyclic selected from the group consisting of 2-thienyl, 3-thienyl, 2-furyl, 3-furyl, 2-pyridyl, 3-pyridyl, and 4-pyridyl wherein said heterocyclic substituent is attached at an available carbon atom and is halogen or lower alkyl of 1 to 4 carbons; $R_6$ is hydrogen or lower alkyl; R₇ is lower alkyl; and X is hydrogen, lower alkanoyloxy,

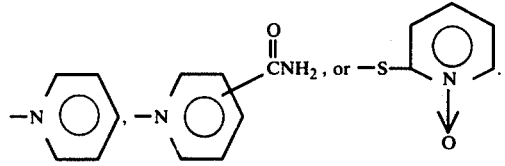

2. The compound of claim 1 wherein R is hydrogen, straight or branched chain alkyl of 1 to 4 carbons, benzyl, phenethyl, diphenylmethyl, trimethylsilyl, 2,2,2-trichloroethyl, an alkali metal ion, an alkaline earth metal ion, dibenzylamine, N,N-dibenzylethylenediamine, methylamine, triethylamine, N-ethylpiperidine, or

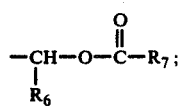

$R_2$ and $R_3$ are independently selected from hydrogen and straight chain alkyl of 1 to 4 carbons, or $R_2$ is hydrogen and $R_3$ is branched chain alkyl of 3 to 4 carbons, phenyl, benzyl, phenethyl, or $R_2$ and $R_3$ taken together with the N-atom to which they are attached form

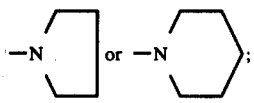

$R_4$ is hydrogen or lower alkyl of 1 to 4 carbons; A is straight or branched chain alkylene of 1 to 4 carbons; $R_5$ is cyclohexadienyl, cyclohexenyl, phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy, and hydroxy, or a mono-substituted or unsubstituted heterocyclic selected from the group consisting of 2-thienyl, 3-thienyl, 2-furyl, 3-furyl, 2-pyridyl, 3-pyridyl, and 4-pyridyl wherein said heterocyclic substituent is attached at an available carbon atom and is chloro, bromo, methyl, or ethyl; $R_6$ is hydrogen or straight or branched chain alkyl of 1 to 4 carbons; $R_7$ is straight or branched chain alkyl of 1 to 4 carbons; and X is hydrogen,

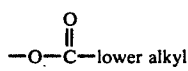

wherein lower alkyl is straight or branched chain of 1 to 4 carbons,

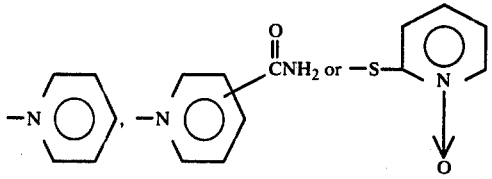

3. The compound of claim 2 wherein X is

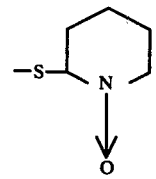

4. The compound of claim 2 having the formula:

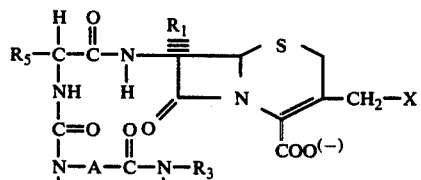

wherein X is

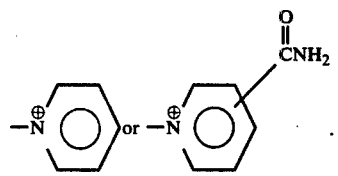

5. The compound of claim 4 wherein X is

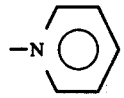

or

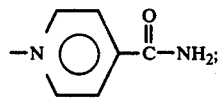

and $R_5$ is 2-thienyl, 3-thienyl, phenyl, or 4-hydroxyphenyl.

6. The compound of claim 2 wherein X is hydrogen or

and lower alkyl is straight or branched chian of 1 to 4 carbons.

7. The compound of claim 3 wherein R is hydrogen, sodium or potassium; $R_5$ is 2-thienyl, 3-thienyl, phenyl, or 4-hydroxyphenyl; $R_2$ and $R_3$ are independently selected from hydrogen, methyl and ethyl; and $R_4$ is hydrogen or methyl.

* * * * *

UNITED STATES PATENT AND TRADEMARK OFFICE
CERTIFICATE OF CORRECTION

PATENT NO. : 4,142,045
DATED : February 27, 1979
INVENTOR(S) : Hermann Breuer et al.

It is certified that error appears in the above-identified patent and that said Letters Patent are hereby corrected as shown below:

Col. 6, line 35, the formula should read: -- $R=N^+=N-$ --.

Col. 9, line 16, "oil residue" should read -- oily residue --.

Col. 26 at Col. III the formula should read:

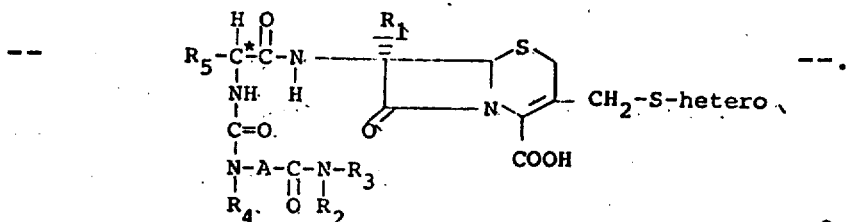

Col. 30, line 15 the formula should read: 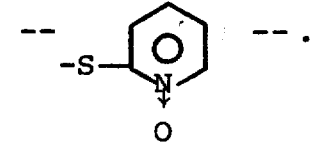

Signed and Sealed this

Fourteenth Day of August 1979

[SEAL]

Attest:

LUTRELLE F. PARKER
Attesting Officer    Acting Commissioner of Patents and Trademarks